United States Patent [19]

Chastain et al.

[11] Patent Number: 5,574,195
[45] Date of Patent: Nov. 12, 1996

[54] METHOD OF PREPARING SELECTED MONOCYCLIC MONOTERPENES

[75] Inventors: Doyle E. Chastain, 137 Birch St., Titusville, Fla. 32780; Naresh Mody, Merritt Island, Fla.; George Majetich, Athens, Ga.

[73] Assignee: Doyle E. Chastain, Titusville, Fla.

[21] Appl. No.: 492,372

[22] Filed: Jun. 19, 1995

[51] Int. Cl.$^6$ .................................................. C07C 35/18
[52] U.S. Cl. ............................................ 568/826; 568/827
[58] Field of Search ..................................... 568/827, 826

Primary Examiner—Samuel Barts
Attorney, Agent, or Firm—Arthur G. Yeager; Earl L. Tyner

[57] ABSTRACT

Process for the preparation of a moncyclic monoterpene having the formula:

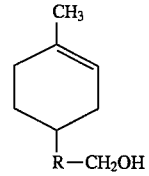

wherein R=—C=CH$_2$ or —CH—CH$_3$.
which comprises treating limonene in a liquid reaction medium with a strong base followed by addition to the medium of a boron-containing reagent to produce a limonenyl adduct. The adduct is cleaved with an oxidizing agent, diluted with water and an organic solvent to produce a two-phase mixture. The monoterpene is recovered from the organic phase.

14 Claims, No Drawings

METHOD OF PREPARING SELECTED MONOCYCLIC MONOTERPENES

TECHNICAL FIELD

This invention relates to a new and useful method of preparing certain allylic alcohols, particularly limonen-10-ol or menth-1-en-9-ol, from limonene; the chemical structures of which are shown below:

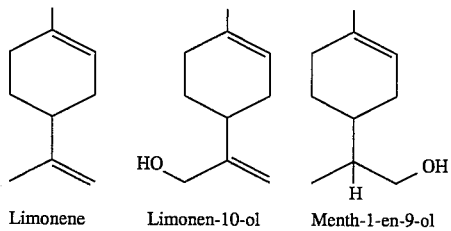

Limonene  Limonen-10-ol  Menth-1-en-9-ol

BACKGROUND OF THE INVENTION

The monoterpene alcohols limonen-10-ol and menth-1-en-9-ol have been found to have a wide spectrum of antimicrobial activity against virtually all bacteria, yeast, and fungi. Because they are readily biodegradable, and are considered environmentally safe, they have numerous potential uses as bactericides and fungicides in agricultural, industrial, pharmaceutical, and consumer products. Both compounds inhibit dental plaque and are likely to be used in mouthwash, toothpaste and chewing gum. Uses as topical and enteric pharmaceutical and veterinary products, preservatives for food, medicine, and cosmetics, antiseptics for food processing equipment, and bactericides and fungicides for agriculture, turf, paint, leather, bathrooms, plastics, air filters, lumber, and industrial cutting oils represent only a few of the potential applications of limonen-10-ol and menth-1-en-9-ol. This invention relates to a new and economical method of producing these allylic alcohols.

Both limonen-10-ol and menth-1-en-9-ol have a mild fruity aroma that is easily flavored. Because they are oils they are insoluble in water, but they are readily emulsified (in water). They are poorly soluble in propylene glycol, and are only sparingly soluble in glycerine. They are soluble in alcohol and are miscible in oil.

Prior art exists for the production of menth 1-en-9-ol. For example, the preparation of menth-1-en-9-ol was unintentionally reported by Vijay, Khanna, and Ladwa in the Indian Journal of Chemistry, Section B 1987, 26B (9), 816–822 in a yield of only 15.5% by the hydroboration/ oxidation of carvone. This method is not an economical method of producing commercial quantities of menth-1-en-9-ol. $BH_3$ is a reagent that easily reduces carbon-carbon double bonds and carbon-oxygen double bonds. In their procedure, the first equivalent of $BH_3$ reduces the carbonyl moiety of carvone to produce intermediate i which is then followed by the addition of $BH_3$ to the C(8), C(9) double bond (cf.ii). However, a small amount of intermediate ii rearranges to form unexpected intermediate iii, and generates a hydride ion. The hydride ion then undergoes a displacement reaction to form the intermediate iv, which upon oxidative workup using hydrogen peroxide and sodium hydroxide furnishes a low yield of menth-1-en-9-ol. Modifications of this reaction procedure gave lower yields of menth-1-en-9-ol. It is unlikely that this procedure can be improved upon to increase the production of menth-1-en-9-ol, and precludes the Khanna and Ladwa method of producing commercial quantities of menth-1-en-9-ol economically. Furthermore, their method, that is summarized below, is totally inapplicable to the production of limonen-10-ol.

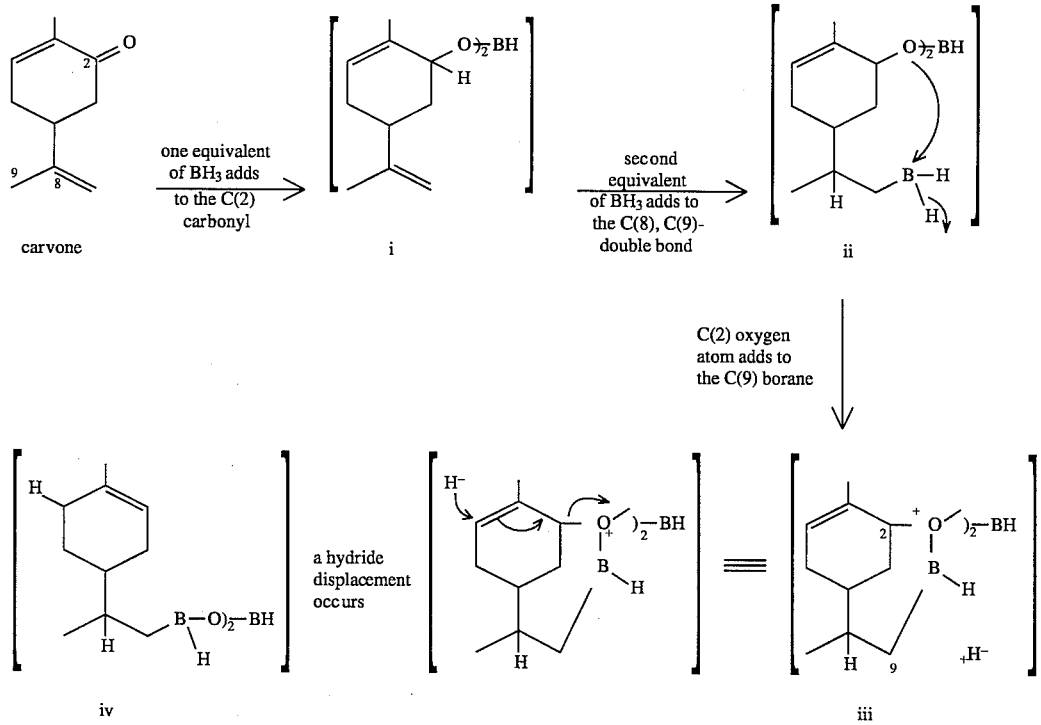

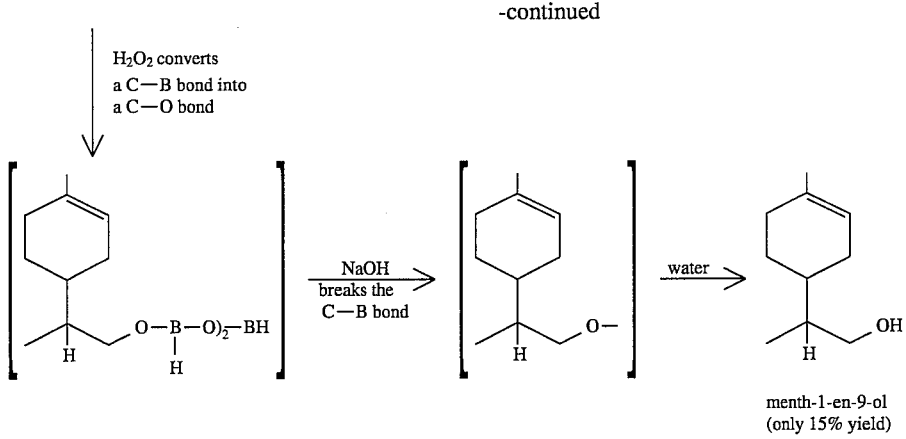

menth-1-en-9-ol
(only 15% yield)

Brown and Zweifel attempted to achieve the monohydroboration of d-limonene with dibonane, but failed as reported in the Journal of the American Chemical Society, 83, 1244 (1961). Similar unsuccessful results were also described by R. Dulou and Chretien-Dessiere in the Bulletin of the Society Chemistry of France, 9, 1362 (1959).

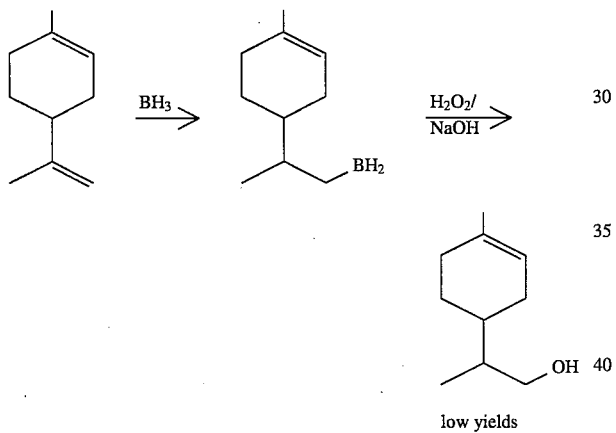

low yields

In the same journal article [JACS, 83, 1244 (1961)] Brown and Zweifel prepared p-menth-1-en-9-ol from limonene in 79% using disiamylborane. While this procedure can be used to produce p-menth-1-en-9-ol on a commercial scale, the cost of the disiamylborane reagent alone makes this a costly process.

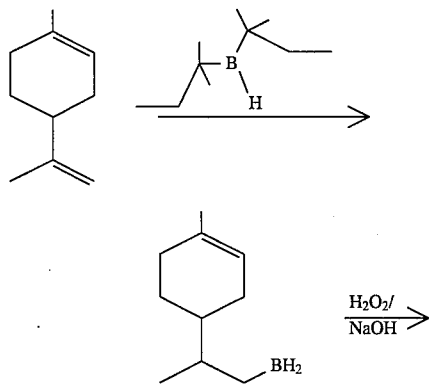

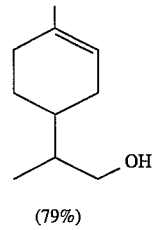

(79%)

The applicants' method of producing menth-1-en-9-ol involves the formation of limonen-10-ol from limonene by the in situ generation of an allylic borate ester, followed by the cleavage of the carbon-boron bond, to produce limonen-10-ol in high yield. Limonen-10-ol was then reduced to menth-1-en-9-ol.

No method of producing limonen-10-ol was uncovered in a search of the literature, but it is recognized that limonene is a cheap material from which numerous natural occurring monoterpenes are derived. For instance limonene is used in the production of perillyl alkanoates as was described by Ansari, Hifzur in Canadian patent 1077959. Carveol can be produced by the oxidation of limonene as was outlined by Bain in U.S. Pat. Nos. 2,863,882 and 3,014,047. Leffingwell (in U.S. Pat. No. 3,538,164) produced limonene-1,2-epoxide from which he derived dihydrocarveol by the addition of small amounts of perchloric acid.

The need to economically supply limonen-10-ol and menth-1-en-9-ol led to this invention that relates to selectively oxidizing Carbon 10 of d-limonene and 1-1limonene to produce limonen-10-ol. Menth-1-en-9-ol is produced by the reduction of limonen-10-ol.

Applicants' invention can be summarized as a method for preparing a monocyclic monoterpene of the formula:

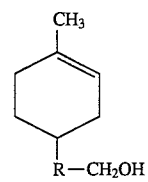

wherein R=—C=CH$_2$ or —CH—CH$_3$

The steps in the process of preparation are described in some detail in the following disclosure for converting limonene to the desired products. In the preparation of limonen-10-ol limonene is treated with a strong base to activate the limonene structure. A boron-containing reagent is then added to produce a limonenyl adduct, i.e., a limonene radical having boron added thereto. An oxidizing agent is then added to remove the boron and introduce an hydroxy group at the 10-position of the limonenyl radical, producing two liquid phases by adding water and an organic solvent to the reaction medium; and recovering limonen-10-ol from the organic phase.

If one wishes to produce menth-1-en-9-ol, the limonen-40-ol is subsequently hydrogenated, reacted with hydrogen gas under subatmospheric pressure in the presence of platinum on activated carbon to produce an essentially pure product of menth-1-en-9-ol in quantitative yield.

The following examples are illustrative of the best mode for carrying out the invention. They are, obviously, not to be construed as limitative of the invention since various other embodiments can readily be evolved in view of the teachings provided herein. In Example 1 the applicants outline their preferred method of producing limonen-10-ol from limonene while Example 2 shows the preferred method of producing menth-1-en-9-ol from the intermediate compound limonen-10-ol. In Example 3 formulations using menth-1-en--ol and limonen-10-ol as bactericides and fungicides are presented.

EXAMPLE 1

The applicants' preferred method of producing limonen-10-ol was to add in a dropwise fashion 100 ml of 10.00 M n-butyl-lithium (1.00 mole, Aldrich) to 700 ml of dry petroleum ether or dry cyclohexane distilled from CaH₂, and then cool the mixture to 0° C. (using an ice bath) and add it dropwise to 150 ml of tetra-methylethylenediamine (TMEDA 1.10 moles) over 5 minutes and then stir it at 0° C. for one hour before 136 grams of d-limonene or 1-1limonene (1.00 mole) was cautiously added to the mixture, warmed to room temperature (20° C.) over six hours and then stirred for sixty hours at room temperature, after which the solution was cooled to −78° C. using an acetone cooling bath (with a low temperature refrigeration unit Neslab Cryocool −80) and then 113 ml (1.4 moles) of trimethyl borate was added over a 90 minute period and then warmed to −30° C. over a two hour period, followed by the dropwise addition of 170 ml of a 30% aqueous hydrogen peroxide solution over a two hour period. The mixture was then diluted with 200 ml of water and 500 ml of diethyl ether. The organic phase was separated and the aqueous phase was twice extracted with 500 ml of diethyl ether. The combined ethereal extract was washed with brine, dried over anhydrous magnesium sulfate, filtered, and then concentrated under reduced pressure (12 mm of Hg) to a crude residue that produced 43 grams of unreacted limonene when distilled under vacuum at 30° C. at 3.00 mm Hg and 98 grams of limonen-10-ol when distilled at 89°–95° C. at 2.5 mm Hg.

The conversion of limonene to limonen-10-ol is represented by the following chemical equation. The numbers in the brackets are ACS registry numbers for the various compounds and reagents cited.

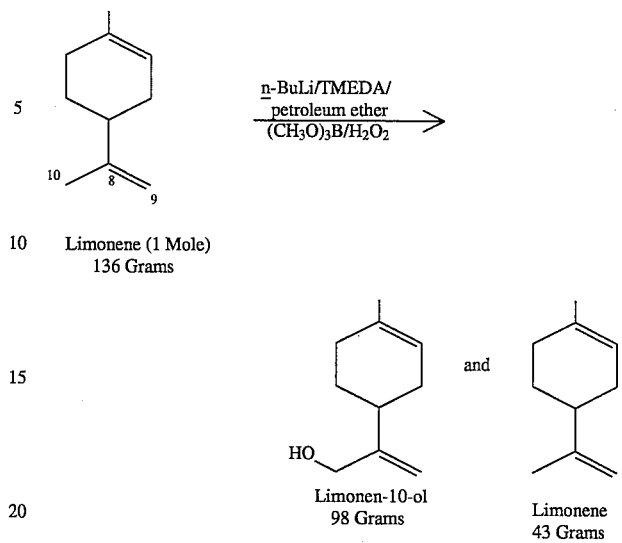

100 ml 10.00 M n-BuLi in hexanes [109-72-8] or Aldrich #23,071-5
700 ml petroleum ether [8032-32-4] or Aldrich #30,0314
150 ml tetramethylethylenediamine [110-18-91 or Aldrich #T2-250-0
113 mo trimethyl borate [121-43-7] or Aldrich #T7-565-5
170 ml 30% aqueous hydrogen peroxide in water [7722-84-1] or Aldrich #21,676-3
136 grams of limonene-Florida Chemical Company, Lake Alfred, Fla.

Although the method appears to be a straightforward procedure for making an anion of an unactivated position, several subtle encounters greatly influence the yield of limonen-10-ol. For example, the reaction temperatures cited and the duration of reaction times are of critical importance. While the initial mixing of the n-butyllithium, TMEDA and limonene were carried out over an hour period at 0° C. for safety reasons, it was determined that more than fifty hours at room temperature were required in order to insure complete allylic anion formation; shorter reaction times or temperatures above room temperature (<25° C.) gave dramatically lower yields of limonen-10-ol. It was also determined to be necessary to add the trimethyl borate slowly to a cold solution of the allylic anion. The temperature of −30° C. was employed as lower reaction temperatures gave lower yields of limonen-10-ol. Warmer temperatures, such as those temperatures cited can vary by +10° C. without significant complications. With the exception of the lengthy reaction time necessary for the formation of the allylic anion, the other reaction times (the rate at which methyl borate is added and the oxidative cleavage of the allylic borate using hydrogen peroxide) do not appear to have critical limits. These reaction times could be safely shortened by as much as half. The use of hexanes or other hydrocarbon solvents (as opposed to petroleum ether or dry cyclohexane) produce lower yields of limonen-10-ol. The use of n-butyllithium in combination with potassium tert-butoxide to generate the allylic carbanion gave poor yields of limonen-10-ol (Pure and Applied Chemistry Vol. 60, pp 1627–34, 1988). Using hydrogen peroxide in quantities greater than the prescribed amount results in unwanted epoxides. Quenching the allylic carbanion with oxygen or dry air results in the formation of a dimer (.shown below) that is difficult to remove and lowers the yield of the desired product. Similar side reactions are known in other chemical processes and are categorized as a "Wurtz coupling". Since the anions of two molecules of limonene are involved, the formation of these byproducts lowers the yield of the desired allylic alcohol. The use of oxygen or dry air to oxidize an allylic cabanion is known to result in a disappointing yield, as reported in the Journal of the American Chemical Society, 1972 (4302). Treatment of the allylic anion with trimethyl borate results in the rapid formation of an allylic borate ester. Virtually no dimer formation is observed. The structure of limonen-10-ol and the Wurtz coupling structure can be identified using proton and carbon nuclear magnetic resonance (NMR), as well as infrared (IR), and mass spectroscopy (MS). The structure of the limonene dimer and the spectral data of limonen-10-ol and the limonene dimer are shown below.

limonene dimer:

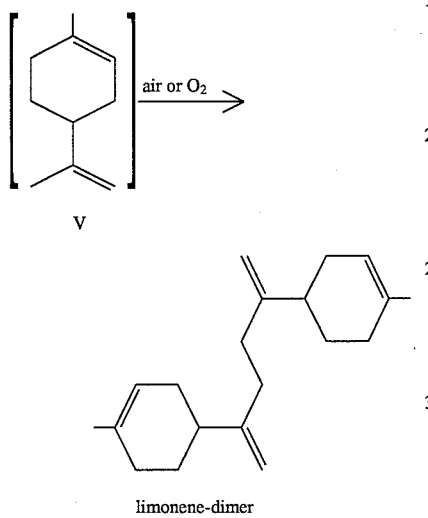

V limonene-dimer $^1$H NMR (CDCl$_3$) δ 1.40–2.30 (m, 13H), 4.70–4.80 (br. s, 2H), 5.35–5.45 (br.s, 1H).
$^{13}$C NMR (CDCl$_3$) 154.2 (s), 133.7 (s), 120.7 (d). 107.1 (t), 39.8 (q), 33.5 (t), 31.4 (t), 30.7 (t), 28.3 (t), 23.4 (q) ppm.
IR (film) 1640 cm$^{-1}$.
MS m/e 270(M$^+$)
Limonen-10-ol:
$^1$H NMR(CDCl$_3$) δ 1.40–2.25 (m, 11H), 4.11 (br. s, 2H), 5.03 (s, 1H), 5.35–5.45 (br. s., 1H).
$^{13}$C NMR (CDCl$_3$) 153.9 (s), 133.8 (s), 120.3 (d), 107.6 (t), 65.0 (t) 36.8 (d), 31.2 (t), 30.4 (t), 28.1 (t), 23.4 (q) ppm.
IR (film) 3347, 1643, 893 cm$^{-1}$.
MS m/e 152 (M$^+$)

A particular advantage of the above outlined method of producing limonen-10-ol is its noticeable lack of side products and its excellent reproducibility. When other hydrocarbon solvents are used the yield of limonen-10-ol is difficult to reproduce and unwanted compounds are generated. Another significant advantage is that no compound other than unreacted limonene is formed and the unreacted limonene is easily recovered.

The in situ formation of an allylic boronate represents a new method of producing a high yield of limonen-10-ol that is important commercially because of its use as a bactericide and fungicide in agricultural, industrial, pharmaceutical and consumer products, and allows such terpene alcohols to serve as intermediate compounds in the production of other terpene compounds.

EXAMPLE 2

Because each terpene alcohol has certain preferred uses that relate to its unique antimicrobial spectrum, it is prudent to economically produce menth-1-en-9-ol for such uses.

The applicants' method of producing menth-1-en-9-ol involves the direct conversion of limonene into limonen-10-ol as was outlined in Example 1 above. In the first step, treatment of limonene using strongly basic conditions (that is, n-butyllithium and tetramethylethylenediamine) generates an allylic carbanion that is reacted with trimethyl borate to produce an allylic borate ester without isolation. Treatment of this intermediate with hydrogen peroxide results in a high yield of limonen-10-ol that is contaminated only by unreacted limonene. Limonen-10-ol can then be hydrogenated in high yield to menth-1-en-9-ol as is depicted below.

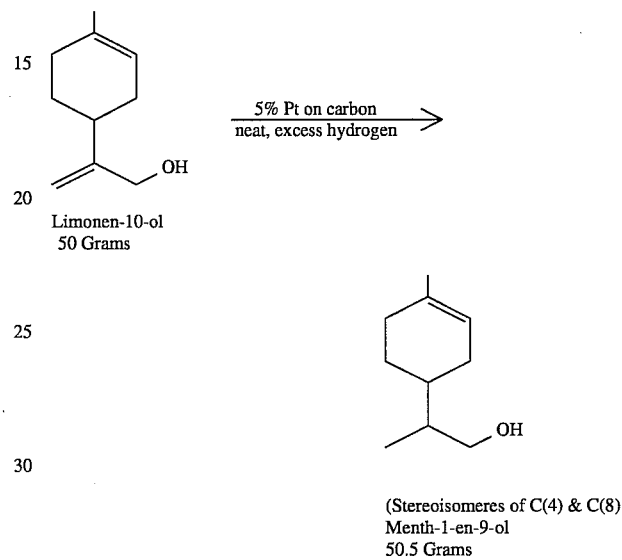

Limonen-10-ol
50 Grams (Stereoisomeres of C(4) & C(8)
Menth-1-en-9-ol
50.5 Grams 0.5 g of platinum on activated carbon Aldrich #20,593-1

The applicants preferred method of producing menth-1-en-9-ol is to charge a Parr-bomb with 50 grams of limonen-10-ol and 0.5 grams of 5% platinum on activated carbon. Using a Parr-shaker$^1$, the reaction vessel is stirred under one atmosphere of hydrogen at 4.5 psi of pressure for 96 hours (4 days). The reaction mixture is then degassed and removed from the hydrogenation apparatus after which the reaction mixture is filtered through a small plug of glass wool to remove the catalyst. Pure menth-1-en-9-ol is produced in a quantitative yield as can be determined by vacuum distillation at 90°–95° C. at 2.5 mm Hg followed by proton and carbon NMR mass spectroscopy, IR, and MS spectroscopy as indicated in the data below.

$^1$Parr Pressure Reaction Apparatus manufactured by Parr Instrument Company, Moline, Ill.

Menth-1-en-9-ol:
$^1$H NMR (CDCl$_3$) δ 0.83–0.93 (m, 3H), 1.10–2.10 (m, 12H), 3.40–3.65 (m, 2H), 5.35 (br. s, 1H).
$^{13}$C NMR (CDCl$_3$) 133.9 (s), 122.7 (d), 120.6 (d), 67.1 (t), 66.2 (t), 40.1 (d), 39.8 (d), 35.6 (d), 30.6 (t), 30.5 (t), 29.7 (t), 27.5 (t), 27.1 (t), 25.3 (t), 23.4 (q), 13.6 (q), 13.1 (q) ppm. Note: this data represents a mixture of diasteromers [a mixture of stereoisomers at C(4) and C(8)] IR (film) 3344, 1499, 1376, 1038 cm$^{-1}$. MS m/e 154 (M$^+$)

The use of other common reduction catalysts was examined including palladium, palladium on various supports, Raney-nickel and platinum on other supports. Five percent platinum on carbon gave complete reduction of the C (8), C(9)-double bond without overreduction of the C(1), C(2)-double bond. This is important as the product (the menth- 1-en-9-ol) and the starting material (the limonen-10-ol) are difficult to separate. At first glance, the reaction time may seem overly long, but carrying out the hydrogenation at higher pressures in an attempt to shorten the reaction time results in over-reduction and the loss of the C(1), C(2)-trisubstituted double bond. The use of solvents to "aid" this hydrogenation slows the reaction.

EXAMPLE 3

In example 3, formulations containing limonen-10-ol and menth-1-en-9-ol are presented. Limonen-10-ol and menth-1-en-9-ol are prepared in the following formulations including solutions, gels, soaps, paints, pastes, creams, ointments, suppositories, tampons, aerosols, and emulsions. When bacteria, yeast, or fungi are treated with formulations that contain limonen-10-ol or menth-1-en-9-ol, the formulations kill or prevent the growth of bacteria, yeast, and fungi.

A. LIQUIDS

1. SOLUTIONS OR SPRAYS

| CHEMICAL | % OF TOTAL | RANGE | ACTION |
|---|---|---|---|
| a. Menth-1-en-9-ol | 1.0% | 0.1–50% | fungicide |
| Corn Oil | 99.0% | 50–99.9% | diluent |
| | 100.0% | | |
| b. Limonen-10-ol | 1.0% | 0.1–50% | bactericide |
| Ethyl Alcohol | 99.0% | 50–99.9% | diluent |
| | 100.0% | | |

2. MOUTHWASH

| CHEMICAL | % OF TOTAL | RANGE | ACTION |
|---|---|---|---|
| a. Menth-1-en-9-ol | 10.0% | 0.1–50% | bactericide |
| Cinnamon oil | 1.0% | 1–5% | flavor |
| Oil of Cloves | 1.0% | 1–5% | flavor |
| Peppermint oil | 1.0% | 1–5% | flavor |
| Ethyl Alcohol | 87.0% | 35–96.9% | diluent |
| | 100.0% | | |

B. DENTIFRICE

1. LIQUID

| CHEMICAL | % OF TOTAL | RANGE | ACTION |
|---|---|---|---|
| Liquid soap concentrate | 5.0% | 2–10% | surfactant |
| Saccharin | 0.2% | 0.1–1.0% | flavor |
| Clove Oil | 1.0% | 0.5–3.0% | flavor |
| Cinnamon Oil | 0.5% | 0.5–3.0% | flavor |
| Peppermint Oil | 0.5% | 0.5–3.0% | flavor |
| Ethyl Alcohol | 82.6% | 29.5–95.3% | diluent |
| Color | 0.2% | 0.1–0.5% | color |
| Limonen-10-ol | 10.0% | 1–50% | bactericide |
| | 100.0% | | |

2. GEL

| CHEMICAL | % OF TOTAL | RANGE | ACTION |
|---|---|---|---|
| Sodium monofluorophosphate | 0.8% | 0.5–1.5% | antiplaque |
| Limonen-10-ol | 15.0% | 1–50% | bactericide |
| Hydrated silica xerogel | 12.0% | 8–15% | abrasive |
| Hydrated thickening silica | 9.5% | 5–10% | binder |
| Sorbitol 70% solution | 49.8% | 5–78.3% | humectant |
| Polyethylene glycol 32 | 6.0% | 3–7% | bodying agent |
| Sodium lauryl sulfate | 1.5% | 1–2% | surfactant |
| Carboxymethyl cellulose gum | 1.0% | 0.5–2% | binder |
| S D alcohol | 1.0% | 0.5–2% | stabilizer |
| Flavor | 3.0% | 2–4% | flavor |
| Saccharin | 0.2% | 0.1–0.5% | flavor |
| F D & C Green #3 | 0.1% | 0.1–0.5% | color |
| F D & C Yellow #10 | 0.1% | 0.1–0.5% | color |
| | 100.0% | | |

3. PASTE

| CHEMICAL | % OF TOTAL | RANGE | ACTION |
|---|---|---|---|
| Sodium monofluorophosphate | 0.8% | 0.5–1.5% | antiplaque |
| Menth-1-en-9-ol | 5.0% | 1–50% | bactericide |
| Dicalcium phosphate dihydrate | 22.0% | 21.6–30% | abrasive |
| Water | 59.0% | 18.2–69.5% | diluent |
| Glycerine | 7.1% | 5.6–12.5% | bodying agent |
| Flavor | 2.0% | 2–3% | flavor |
| Sodium lauryl sulfate | 1.5% | 1–2% | surfactant |
| Carboxymethyl cellulose gum | 1.4% | 0.5–2.0% | binder |
| Tetrasodium pyrophosphate | 1.0% | 0.5–2.0% | binder |
| Sodium saccharin | 0.2% | 0.1–0.5% | flavor |
| | 100.0% | | |

C. OINTMENTS & SUPPOSITORIES WITH AND WITHOUT HYDROCORTISONE

1. OINTMENT WITH HYDROCORTISONE

| CHEMICAL | % OF TOTAL | RANGE | ACTION |
|---|---|---|---|
| Menth-1-en-9-ol | 1.0% | 0.1–15.0% | bactericide |
| Polyethylene glycol 3350 | 59.0% | 48.5–59.7% | bodying agent & emulsifier |
| Polyethylene glycol 400 | 39.0% | 31.5–39.7% | bodying agent & emulsifier |
| Hydrocortisone | 1.0% | 0.5–5.0% | anti-inflammatory |
| | 100.0% | | |

2. OINTMENT WITHOUT HYDROCORTISONE

| CHEMICAL | % OF TOTAL | RANGE | ACTION |
|---|---|---|---|
| Menth-1-en-9-ol | 1.0% | 0.1–15.0% | anti-yeast |
| Polyethylene glycol 3350 | 59.5 | 51.0–59.95% | bodying agent & emulsifier |
| Polyethylene glycol 400 | 39.5% | 34.0–39.95% | bodying agent & emulsifier |
| | 100.0% | | |

3. SUPPOSITORY WITHOUT HYDROCORTISONE

| CHEMICAL | % OF TOTAL | RANGE | ACTION |
|---|---|---|---|
| Menth-1-en-9-ol | 0.1% | 0.1–15% | fungicide |
| Polyethylene glycol 1000 | 63.4% | 50.0–64.9% | bodying agent & emulsifier |
| Polyethylene | 46.5% | 35.0–49.9% | bodying |

4. SUPPOSITORY WITH HYDROCORTISONE

| Ingredient | % | Range | Function |
|---|---|---|---|
| (continued) glycol 3350 | | | agent & emulsifier |
| | 100.0% | | |
| Limonen-10-ol | 1.0% | 0.1–15% | anti-yeast |
| Polyethylene glycol 1000 | 74.0% | 60.0–75.2% | bodying agent & emulsifier |
| Polyethylene glycol 3350 | 24.0% | 20.0–24.2% | bodying agent & emulsifier |
| Hydrocortisone | 1.0% | 0.5–5.0% | anti-inflammatory |
| | 100.0% | | |

D. CREAMS WITHOUT HYDROCORTISONE

| Ingredient | % | Range | Function |
|---|---|---|---|
| Menth-1-en-9-ol | 1.0% | 0.1–15.0% | bactericide |
| Cetyl alcohol | 15.0% | 12.0–18.0% | thickener |
| Arlacel 165 ** | 5.0% | 3.5–7.5% | emulsifier |
| Sorbitol 70% solution | 5.5% | 3.5–8.0% | humectant |
| Water | 73.5% | 51.5–80.9% | diluent |
| | 100.0% | | |
| Limonen-10-ol | 1.0% | 0.1–15.0% | anti-yeast |
| Spermaceti wax | 12.5% | 10.0–15.0% | thickener |
| Sorbitan monostearate | 10.0% | 7.5–12.5% | emulsifier |
| Polyethylene 20 Sorbitan monostearate | 6.0% | 4.0–8.0% | emulsifier |
| Water | 75.5% | 49.5–78.4% | diluent |
| | 100.0% | | |

E. CREAMS WITH HYDROCORTISONE

| Ingredient | % | Range | Function |
|---|---|---|---|
| Menth-1-en-9-ol | 1.0% | 0.1–15.0% | fungicide |
| Cetyl alcohol | 15.0% | 12.0–18.0% | thickener |
| Arlacel 165 ** | 5.0% | 3.5–7.5% | emulsifier |
| Sorbitol 70% solution | 5.0% | 3.5–8.0% | humectant |
| Hydrocortisone | 1.0% | 0.5–5.0% | anti-inflammatory |
| Water | 73.0% | 46.5–80.4% | diluent |
| | 100.0% | | |

\* Croda, Inc., 51 Madison Ave., New York, New York 10010
\*\* Glycerol monostearate and polyoxyethylene stearate ICI of America (Formerly Atlas Chemical Industries), Wilmington, Delaware 19899

F. TAMPONS

| Ingredient | % | Range | Function |
|---|---|---|---|
| Menth-1-en-9-ol (2 cc) 2 Gm | 8.0% | 1–15% | bactericide |
| Tampon 23 Gm | 92.0% | 85–99% | reservoir for bactericide |
| | 100.0% | | |

G. AEROSOLS WITHOUT HYDROCORTISONE

| Ingredient | % | Range | Function |
|---|---|---|---|
| (1) Menth-1-en-9-ol | 5.0% | 0.5–50% | fungicide |
| Ethyl alcohol | 95.0% | 50–99.5% | diluent |
| | 100.0% | | |

Pressurized nitrogen propellant at 100–125 psig

| Ingredient | % | Range | Function |
|---|---|---|---|
| (2) Limonen-10-ol | 10.0% | 0.5–50.0% | anti-yeast |
| Soybean Oil | 90.0% | 50.0–99.5% | diluent |
| | 100.0% | | |

Pressurized nitrogen propellant at 100–125 psig

H. AEROSOL WITH HYDROCORTISONE

| Ingredient | % | Range | Function |
|---|---|---|---|
| Limonen-10-ol | 10.0% | 0.5–50% | bactericide |
| Soybean oil | 98.0% | 45–99.0% | diluent |
| Hydrocortisone | 1.0% | 0.5–5.0% | anti-inflammatory |
| | 100.0% | | |

Pressurized nitrogen propellant at 100–125 psig

I. OIL IN WATER EMULSION

| Ingredient | % | Range | Function |
|---|---|---|---|
| (1) Menth-1-en-9-ol | 0.1% | 0.1–50% | fungicide |
| (2) Corn oil | 10.0% | 10–15% | oil |
| (2) Arlacel 40** | 2.0% | 1–3% | emulsifier |
| (2) Tween 40 | 3.0% | 2–4% | emulsifier |
| (3) Water | 84.9% | 28–86.9% | diluent |
| | 100.0% | | |

Heat (2) to 70° C. Heat (3) to 72° C. Add (3) to (2) with continuous agitation. When (3) and (2) cool to 40° C., add (1) with continuous agitation until room temperature is reached.

J. OIL IN WATER EMULSION WITH SOAP (FUNGICIDAL OR BACTERICIDAL SOAP)

| Ingredient | % | Range | Function |
|---|---|---|---|
| (1) Limonen-10-ol | 1.0% | 0.1–25% | bactericide |
| (2) Corn oil | 30.0% | 20.0–40.0% | oil |
| (2) Arlacel 40** | 2.0% | 1.0–3.0% | emulsifier |
| (2) Tween 40 | 3.0% | 2.0–4.0% | emulsifier |
| (2) Liquid soap concentrate | 3.5% | 2.5–5.0% | surfactant |
| (3) Water | 60.5% | 23–74.4% | diluent |
| | 100.0% | | |

Heat (2) to 70° C. Heat (3) to 72° C. Add (3) to (2) with continuous agitation. When (3) and (2) cool to 40° C., add (1) with continuous agitation until room temperature is reached.

K. WATER IN OIL EMULSION

| Ingredient | % | Range | Function |
|---|---|---|---|
| (1) Menth-1-en-9-ol | 1.0% | 0.1–25% | anti-yeast |
| (2) Arlacel 186** | 3.0% | 2.0–4.0% | emulsifier |
| (2) Soybean oil | 15.0% | 10.0–25.0% | oil |
| (2) Ceresin wax | 0.5% | 0.3–0.6% | thickener |
| (2) Beeswax | 0.5% | 0.3–0.6% | thickener |
| (2) Tween 80 | 0.5% | 0.3–0.6% | emulsifier |
| (3) Water | 79.5% | 44.2–87.0% | diluent |
| | 100.0% | | |

Heat (2) to 70° C. Heat (3) to 72° C. Add (3) to (2) with continuous agitation. When (3) and (2) cool to 40° C., add (1) with continuous agitation until room temperature is reached.

L. PAINT

1. ENAMEL

| Ingredient | % | Range | Function |
|---|---|---|---|
| Menth-1-en-9-ol | 1.00% | 1–10% | fungicide |
| Titanium dioxide | 14.91% | 12–16% | pigment |
| Calcium carbonate | 29.83% | 25–35% | pigment |

-continued

| | | | |
|---|---|---|---|
| Silicate | 4.81% | 3–6% | pigment |
| Soya alkyd resin | 25.72% | 22–28% | pigment (binder) |
| Mineral spirits | 23.73% | 5–37% | solvent (thinner) |
| | 100.00% | | |
| 2. LATEX | | | |
| Limonen-10-ol | 1.0% | 1–10% | fungicide |
| Titanium dioxide | 10.76% | 8–12% | pigment |
| Silicate | 12.91% | 10–16% | pigment |
| Calcium carbonate | 20.91% | 15–25% | pigment |
| Vinyl acrylic resin solids | 12.22% | 10–16% | vehicle (binder) |
| Glycol | 8.30% | 6–10% | solvent (thinner) |
| Water | 34.00% | 12–50% | solvent (thinner) |
| | 100.00% | | |

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what it is desired to secure by Letters Patent of the United States is:

1. Process for the preparation of a monocyclic monoterpene having the formula:

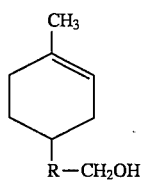

wherein R=—C=CH$_2$
which comprises treating limonene in a liquid reaction medium with a strong base followed by addition to the medium of a boron-containing reagent to produce a limonenyl adduct; treating the adduct with an oxidizing agent to cause cleavage of said adduct and the introduction of an hydroxyl group at the 10-position of said limonenyl structure; diluting said medium with water and an organic solvent to produce two liquid phases, and recovering from the organic phase limonen-10-ol having the above formula when R=—C=CH$_2$.

2. The process of claim 1 which additionally comprises hydrogenating said limonen-10-ol and recovering menth-1-en-9-ol having the above formula when R=C—CH$_3$.

3. The process of claim 1 wherein said boron reagent is trimethylborate.

4. The process of claim 1 wherein said oxidizing agent is hydrogen peroxide.

5. Process for preparing a monocyclic monoterpene having the formula:

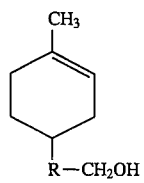

wherein R=—C=CH$_2$
which comprises the following sequential steps:

1. adding n-butyllithium to dry petroleum ether to obtain Mixture A;
2. adding Mixture A to TMEDA (tetramethylenediamine) to obtain Mixture B;
3. adding d- or l-llimonene to Mixture B to obtain Mixture C;
4. adding trimethylborate to Mixture C to obtain Mixture D;
5. adding H$_2$O$_2$ to Mixture D and diluting with water and diethyl ether and allowing the diluted mixture to separate into an organic phase and an aqueous phase;
6. extracting the aqueous phase with diethyl ether to give additional organic portions that are added to said organic phase;
7. washing, drying and concentrating the combined organic phase to produce a crude mix of unreacted limonene and limonen-10-ol having the above formula when R=—C=CH$_2$.

6. Process of claim 5 which additionally comprises reacting said crude product of step 7 with hydrogen at superatmospheric pressure in presence of platinum on activated carbon to produce menth-1-en-9-ol having above formula when R=CH—CH$_3$.

7. The process of claim 5 wherein step 1 is carried out employing 1 mol of 10.0 M butyllithium per 700 ml of said dry petroleum ether.

8. The process of claim 5 wherein said Mixture A is cooled to about 0° C. before adding it dropwise to TMEDA in step 2.

9. The process of claim 5 wherein said Mixture B is stirred at about 0° C. for about one hour before said d- or l-llimonene is added, and then warmed to room temperature.

10. The process of claim 5 wherein Mixture C is cooled to about −78° C. immediately before said addition of trimethylborate, and thereafter is warmed to about −30° C.

11. The process of claim 5 wherein the dilutents in step 5 are present in the volume ratio of about five parts water to seven parts ether.

12. The process of claim 5 wherein said washing, drying, and concentrating in step 7 includes washing with brine, drying over anhydrous magnesium sulfate, and filtration under subatmospheric pressure.

13. The process of claim 5 wherein said crude mix of limonen-10-ol and unreacted limonene comprises about 65–75% by weight limonen-10-ol.

14. The process of claim 6 wherein said crude product is stirred under hydrogen gas at about 4.5 psi pressure for about four days time.

* * * * *